United States Patent
Ohashi et al.

(10) Patent No.: US 10,457,625 B2
(45) Date of Patent: Oct. 29, 2019

(54) TREATMENT METHOD OF COMPOSITION CONTAINING FLUORINE-CONTAINING ORGANIC ACID HAVING CARBON NUMBER OF 2 TO 7 AND IMPURITIES

(71) Applicant: DAIKIN INDUSTRIES, LTD., Osaka-shi, Osaka (JP)

(72) Inventors: Mihoko Ohashi, Settsu (JP); Shuji Itatani, Settsu (JP); Atsuko Tai, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/768,859

(22) PCT Filed: Oct. 13, 2016

(86) PCT No.: PCT/JP2016/080340
§ 371 (c)(1),
(2) Date: Apr. 17, 2018

(87) PCT Pub. No.: WO2017/069034
PCT Pub. Date: Apr. 27, 2017

(65) Prior Publication Data
US 2019/0055185 A1    Feb. 21, 2019

(30) Foreign Application Priority Data
Oct. 19, 2015    (JP) .................................. 2015-205717

(51) Int. Cl.
*C07C 51/47*    (2006.01)
*C07C 51/48*    (2006.01)

(52) U.S. Cl.
CPC .............. *C07C 51/47* (2013.01); *C07C 51/48* (2013.01)

(58) Field of Classification Search
CPC ................................. C07C 51/47; C07C 51/48
See application file for complete search history.

(56) References Cited

U.S. PATENT DOCUMENTS

| | | |
|---|---|---|
| 2010/0197964 A1 | 8/2010 | Kuramitsu |
| 2012/0029232 A1 | 2/2012 | Kuramitsu et al. |
| 2014/0187816 A1 | 7/2014 | Aida et al. |

FOREIGN PATENT DOCUMENTS

| | | |
|---|---|---|
| JP | 2015-17111 A | 1/2015 |
| WO | 2009-031562 A1 | 3/2009 |
| WO | 2010/113720 A1 | 10/2010 |
| WO | 2013/038990 A1 | 3/2013 |

OTHER PUBLICATIONS

International Preliminary Report on Patentability and Translation of Written Opinion in International Application No. PCT/JP2016/080340, dated May 3, 2018.
International Search Report for PCT/JP2016/080340 dated Dec. 27, 2016 [PCT/ISA/210].
Communication dated May 10, 2019 from the European Patent Office in application No. 16857349.1.

*Primary Examiner* — Sikarl A Witherspoon
(74) *Attorney, Agent, or Firm* — Sughrue Mion, PLLC

(57) ABSTRACT

A treatment method of at least partially removing impurities from a composition containing a fluorine-containing organic acid having the carbon number of 2 to 7 and impurities, the method including a flocculant mixing step of mixing the composition and a flocculant; and a separating step of separating a mixed phase obtained at the mixing step into a solid phase and a liquid phase.

20 Claims, No Drawings

TREATMENT METHOD OF COMPOSITION CONTAINING FLUORINE-CONTAINING ORGANIC ACID HAVING CARBON NUMBER OF 2 TO 7 AND IMPURITIES

CROSS REFERENCE TO RELATED APPLICATIONS

This application is a National Stage of International Application No. PCT/JP2016/080340, filed on Oct. 13, 2016, which claims priority from Japanese Patent Application No. 2015-205717, filed on Oct. 19, 2015.

FIELD OF THE INVENTION

The present invention relates to a treatment method of at least partially removing impurities from a composition containing a fluorine-containing organic acid having the carbon number of 2 to 7 and impurities.

BACKGROUND OF THE INVENTION

In emulsion polymerization of polymers, an emulsifier is used. For example, in a process of producing a fluoropolymer by homopolymerization or copolymerization of fluorine-containing monomers, a fluorine-containing organic acid such as a fluorocarboxylic acid is used as an emulsifier. Considering the fact that a fluorine-containing organic acid such as a fluorocarboxylic acid is generally expensive and have an effect on the environment, it is usually desirable to recover the fluorine-containing organic acid.

WO 2013/038990 (Patent Document 1) describes a method of recovering an anionic fluorine-containing emulsifier by eluting and recovering an anionic fluorine-containing emulsifier as an acid of the anionic fluorine-containing emulsifier from a base-type ion-exchange resin having adsorbed the anionic fluorine-containing emulsifier. It is described in Patent Document 1 that according to this method, the acid of the anionic fluorine-containing emulsifier used in production of fluoropolymers can be recovered with a high yield and that the acid of the recovered anionic fluorine-containing emulsifier can directly be used for emulsion polymerization of fluoropolymers.

WO 2010/113720 (Patent Document 2) describes a method of adsorbing a fluorocarboxylic acid in which a fluorocarboxylic acid is adsorbed to activated carbon by contacting a liquid containing a fluorocarboxylic acid having an ether bond with the activated carbon. It is described in patent document 2 that a fluorocarboxylic acid having an ether bond can efficiently and selectively be removed from a liquid phase such as factory wastewater, domestic wastewater, and rivers.

DESCRIPTION OF THE RELATED ART

Patent Documents

Patent Document 1: WO 2013/038990
Patent Document 2: WO 2010/113720

SUMMARY OF THE INVENTION

Problem to be Solved by the Invention

A means of recovering a fluorine-containing organic acid such as a fluorocarboxylic acid or a fluorosulfonic acid, for example, has been conventionally studied. On the other hand, a composition containing a fluorine-containing organic acid obtained by recovery generally contains various impurities. A problem to be solved by the present invention is to provide a treatment method of at least partially removing impurities from a composition containing a fluorine-containing organic acid having the carbon number of 2 to 7 and impurities obtained by recovery, for example.

Means for Solving Problem

To solve the problem, the present invention provides the following aspects.

A treatment method of at least partially removing impurities from a composition containing a fluorine-containing organic acid having the carbon number of 2 to 7 and impurities, the method including:
a flocculant mixing step of mixing the composition and a flocculant; and
a separating step of separating a mixed phase obtained at the mixing step into a solid phase and a liquid phase.

A treatment method of at least partially removing impurities from a composition containing a fluorine-containing organic acid having the carbon number of 2 to 7 and impurities, the method including:
a contacting step of contacting the composition with activated carbon; and
a separating step of separating a contacting mixed phase obtained at the step into a solid phase and a liquid phase.

The treatment methods may be performed independently of each other or in combination. When performed in combination, the treatment methods may be performed in any order.

Effect of the Invention

By using the method of the present invention, impurities can at least partially be removed from a composition containing a fluorine-containing organic acid having the carbon number of 2 to 7 (e.g., a composition obtained by recovery of a fluorine-containing organic acid). The method of the present invention can effectively remove, particularly from a composition obtained by recovery etc. of a fluorine-containing organic acid, for example, impurities containing an organic compound having the carbon number of 3 to 50, more specifically, impurities containing one or more selected from the group consisting of a carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50.

DETAILED DESCRIPTION OF THE INVENTION

A treatment method in the present invention is a method of at least partially removing impurities from a composition containing a fluorine-containing organic acid having the carbon number of 2 to 7 and impurities. The method of the present invention will now be described in detail.

Fluorine-Containing Organic Acid Having the Carbon Number of 2 to 7

The fluorine-containing organic acid having the carbon number of 2 to 7 contained in a composition in the method of the present invention may be a fluorine-containing carboxylic acid having the carbon number of 2 to 7 and a salt thereof, and a fluorine-containing sulfonic acid having the carbon number of 2 to 7 and a salt thereof.

The fluorine-containing carboxylic acid having the carbon number of 2 to 7 may be a compound represented by Formula (i):

  (i)

[wherein X is H, F, or Cl, Rf is a linear or branched fluoroalkylene group having the carbon number of 1 to 6, a group having the carbon number of 1 to 6 having a monooxyfluoroalkylene group, or a group having the carbon number of 1 to 6 having a polyoxyfluoroalkylene group].

The linear or branched fluoroalkylene group having the carbon number of 1 to 6 in the Rf group may be, for example, $CF_2$, $C_2F_4$, $C_3F_6$, $C_4F_8$, $C_5F_{10}$, $C_6F_{12}$, CHF, $C_2F_3H$, $C_2F_2H_2$, $C_2FH_3$, $C_3F_5H$, $C_3F_4H_2$, $C_3F_3H_3$, $C_3F_2H_4$, $C_3F_1H_5$, $C_4F_6H_2$, $C_4F_5H_3$, $C_4F_4H_4$, $C_4F_3H_5$, $C_4F_2H_6$, $C_4FH_7$, $C_5F_9H$, $C_5F_3H_2$, $C_5F_7H_3$, $C_5F_6H_4$, $C_5F_5H_5$, $C_5F_4H_6$, $C_5F_3H_7$, $C_5F_2H_9$, $C_5FH_9$, $C_6F_{11}H$, $C_6F_{10}H_2$, $C_6F_9H_3$, $C_6F_8H_4$, $C_6F_7H_5$, $C_6F_6H_6$, $C_6F_5H_7$, $C_6F_4H_8$, $C_6F_3H_9$, $C_6F_2H_{10}$, and $C_6FH_{11}$.

The group having the carbon number of 1 to 6 having a mono oxyfluoroallcylene group and a group having the carbon number of 1 to 6 having a polyoxyfluoroalkylene group in the Rf group may be groups represented by, for example, $(CF_2)_l—(CF_2OCF_2)_m—(CF_2OCF(CF_3))_n$,  Formula (a)

$(CF_2)_l—(CHFOCF_2)_m—(CF_2OCF(CF_3))_n$,  Formula (b)

$(CF_2)_l—(CF_2OCHF)_m—(CF_2OCF(CF_3))_n$,  Formula (c)

$(CHF)_l—(CF_2OCF_2)_m—(CF_2OCF(CF_3))_n$,  Formula (d)

$(CHF)_l—(CHFOCF_2)_m—(CF_2OCF(CF_3))_n$,  Formula (e)

and $(CHF)_l—(CF_2OCHF)_m—(CF_2OCF(CF_3))_n$  Formula (f)

[in the formulae, l is 0 or an integer of 1 to 4, m is 0 or an integer of 1 to 3, and n is 0, 1, or 2, provided that 1+2m+3n does not exceed 6 and that the case of both m and n being 0 is excluded].

In the formulae, it is defined that repeating units enclosed in the parentheses are present in arbitrary order.

In Formula (i), more preferably, X is H or F, and Rf is a group having the carbon number of 1 to 6 having a monooxyfluoroallcylene group, or a group having the carbon number of 1 to 6 having a polyoxyfluoroallcylene group.

The fluorine-containing carboxylic acid having the carbon number of 2 to 7 may more preferably be a perfluorocarboxylic acid represented by Formula (i-a):

X—Rf—COOH  (i-a)

[wherein X is H or F, Rf is a group represented by Formula (a):

$(CF_2)_l—(CF_2OCF_2)_m—(CF_2OCF(CF_3))_n$,  Formula (a)

and in Formula (a), l is 0 or an integer of 1 to 4, m is 0 or an integer of 1 to 3, and n is 0, 1, or 2, provided that 1+2m+3n does not exceed 6, that the case of both m and n being 0 is excluded, and that repeating units enclosed in the parentheses are present in arbitrary order].

In the fluorine-containing carboxylic acid, the carbon number may preferably be 3 to 7, more preferably 5 to 7, and particularly preferably 6 to 7.

The fluorine-containing carboxylic acid having the carbon number of 5 to 7 in a preferred form can be exemplified by, for example, $CF_3OCF(CF_3)CF_2OCF(CF_3)COOH$, $CF_3CF_2OCF_2CF_2OCF_2COOH$, $CF_3OCF_2CF_2CF_2OCHFCF_2COOH$, $CF_3CF_2OCF_2CF_2OCF_2COOH$, $CF_3CF_2OCF_2CF_2OCF_2COOH$, $CF_3OCF_2CF_2CF_2OCHFCF_2COOH$, $CF_3OCF_2CF_2CF_2OCHFCF_2COOH$, $CF_3(CF_2)_4COOH$, $CF_3CF_2CF_2OCF(CF_3)COOH$, $H(CF_2)_6COOH$, $H(CF_2)_4COOH$, and $CH_2=CFCF_2OCF(CF_3)COOH$.

The fluorine-containing sulfonic acid having the carbon number of 2 to 7 may be, for example, a perfluoropropanesulfonic acid, a perfluorobutanesulfonic acid, a perfluorohexanesulfonic acid, $CF_2=CFOCF_2CF_2SO_3H$, and $CF_2=CFOCF_2CF(CF_3)OCF_2CF_2SO_3H$.

The salts of the fluorine-containing carboxylic acid and the fluorine-containing sulfonic acid may be salts having a monovalent cation as a counter ion, for example, alkali metal salts such as potassium salts and sodium salts, ammonium salts, and amine salts (e.g., alkylamine salts such as methylamine, dimethyl amine, trimethylamine, ethylamine, and diethylamine, triethylamine).

A content of a divalent metal salt contained in the composition before treatment in the present invention is preferably 1000 ppm or less, more preferably 100 ppm or less, based on the weight of the composition.

Impurities

The impurities contained in the composition in the method of the present invention may be arbitrary impurities. The impurity may be impurities containing an organic compound having the carbon number of 3 to 50. The organic compound having the carbon number of 3 to 50 may be, for example, one or more selected from a carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50. The carbon number of the organic compound may preferably be in a range of 10 to 40, more preferably in a range of 14 to 35.

The derivatives of the carboxylic acid having the carbon number of 8 to 50 may typically be carboxylic acid ester. The carboxylic acid having the carbon number of 8 to 50 and derivatives thereof may be an aromatic carboxylic acid having the carbon number of 8 to 50 and ester thereof, for example, phthalic acid, phthalic anhydride, phthalimide, phthalate (e.g., sodium salt or potassium salt), phthalic acid mono- or di-alkyl ester (e.g., dimethyl phthalate, diethyl phthalate, diallyl phthalate, dibutyl phthalate, diisobutyl phthalate, di-normal-hexyl phthalate, bis(2-ethylhexyl) phthalate, di-normal-octyl phthalate, di-isononyl phthalate, di-nonyl phthalate, di-isodecyl phthalate, and bis-butyl benzyl phthalate), benzoic acid, benzoic acid alkyl ester (e.g., methyl benzoate, ethyl benzoate, propyl benzoate, and butyl benzoate), salicylic acid, salicylic acid alkyl ester (e.g., methyl salicylate, ethyl salicylate, propyl salicylate, and butyl salicylate), gallic acid, gallic acid alkyl ester (e.g., methyl gallate, ethyl gallate, propyl gallate, and butyl gallate), mellitic acid, mellitic anhydride, cinnamic acid, cinnamic anhydride, cinnamic acid alkyl ester (e.g., methyl cinnamate, ethyl cinnamate, propyl cinnamate, and butyl cinnamate), and fluorinated compounds thereof, aliphatic carboxylic acid having the carbon number of 8 to 50 and ester thereof, for example, octanoic acid, nonanoic acid, decanoic acid, dodecanoic acid, tetradecanoic acid, hexadecanoic acid, heptadecanoic acid, octadecanoic acid, oleic acid, linoleic acid, linolenic acid, arachidonic acid, eicosapentaenoic acid, docosahexaenoic acid, $CF_3(CF_2)_6COOH$, $CF_3(CF_2)_8COOH$, $H(CF_2)_8COOH$, $H(CF_2)_{10}COOH$, $CF_3CF_2CF_2OCF(CF_3)CF_2OCF(CF_3)COOH$, etc., and alkyl ester thereof (e.g., methyl ester, ethyl ester, propyl ester, and butyl ester and the like). The carbon number of the carboxylic acid and derivatives thereof may preferably be in a range of 10 to 40, more preferably in a range of 14 to 35.

The hydrocarbon having the carbon number of 8 to 50 may be a linear, branched, or alicyclic, saturated or unsaturated hydrocarbon having the carbon number of 8 to 50. The carbon number may more preferably be 10 to 40, further preferably 20 to 40. The saturated hydrocarbon is sometimes referred to as paraffin.

The phenol having the carbon number of 6 to 50 may be a monohydric or polyhydric phenol compound having the carbon number of 6 to 50, for example, phenol, di-t-butylphenol, cresol, naphthol, hydroquinone, catechol, resorcinol, pyrogallol, phloroglucinol, and hexahydroxybenzene and the like.

The alcohol having the carbon number of 3 to 30 may be, for example, propan-1-ol, butan-1-ol, pentan-1-ol, hexan-1-ol, heptan-1-ol, nonan-1-ol, decan-1-ol, undecan-1-ol, dodecan-1-ol, tridecan-1-ol, tetradecan-1-ol, pentadecan-1-ol, hexadecan-1-ol, heptadecan-1-ol, octadecan-1-ol, nonadecan-1-ol, icosan-1-ol, heneicosan-1-ol, docosan-1-ol, tricosan-1-ol, tetracosan-1-ol, pentacosan-1-ol, hexacosan-1-ol, heptacosan-1-ol, octacosan-1-ol, nonacosan-1-ol, triacontan-1-ol, policosanol, 2-methylpropan-1-ol, 3-methylbutan-1-ol, propan-2-ol, butan-2-ol, pentan-2-ol, hexan-2-ol, heptan-2-ol, 2-methylbutan-1-ol, cyclohexanol, 2-methylpropan-2-ol, 2-methylbutan-2-ol, 2-methylpentan-2-ol, 2-methylhexan-2-ol, 2-methylheptan-2-ol, 3-methylpentan-3-ol, 3-methyloctan-3-ol, ethylene glycol, glycerin, hydroquinone, catechol, and 4-t-butyl catechol and the like.

The polyether having the carbon number of 8 to 50 may be, for example, polyether polyols having the carbon number of 8 to 50, such as polyethylene glycol having the carbon number of 8 to 50, polypropylene glycol having the carbon number of 8 to 50, and polyethylene/polypropylene glycol having the carbon number of 8 to 50 ("polyethylene/polypropylene" means a group composed of an oxyethylene portion and an oxypropylene portion);

poly(oxyalkylene) alkyl ether having the carbon number of 8 to 50, such as poly(oxyethylene) monoalkyl ether having the carbon number of 8 to 50, poly(oxyethylene) dialkyl ether having the carbon number of 8 to 50, poly(oxypropylene) monoalkyl ether having the carbon number of 8 to 50, poly(oxypropylene) dialkyl ether having the carbon number of 8 to 50, poly(oxyethylene)/(oxypropylene) monoalkyl ether having the carbon number of 8 to 50, and poly(oxyethylene)/(oxypropylene) dialkyl ether having the carbon number of 8 to 50 (in the above description, "(oxyethylene)/(oxypropylene)" means a group composed of an oxyethylene portion and an oxypropylene portion); and poly(oxyalkylene) arylalkyl ether having the carbon number of 8 to 50, such as poly(oxyethylene) monoarylalkyl ether having the carbon number of 8 to 50, poly(oxyethylene) diarylalkyl ether having the carbon number of 8 to 50, poly(oxypropylene) monoarylalkyl ether having the carbon number of 8 to 50, poly(oxypropylene) diarylalkyl ether having the carbon number of 8 to 50, poly(oxyethylene)/(oxypropylene) monoarylalkyl ether having the carbon number of 8 to 50, and poly(oxyethylene)/(oxypropylene) diarylalkyl ether (in the above description, "(oxyethylene)/(oxypropylene)" means a group composed of an oxyethylene portion and an oxypropylene portion).

The method of the present invention can significantly be used as a method of at least partially removing impurities such as liquid impurities and water-soluble or amphiphilic organic impurities having been considered as being difficult to remove with conventional methods.

The liquid impurities may be, for example, phthalic acid dialkyl ester (dimethyl phthalate, diethyl phthalate, diallyl phthalate, dibutyl phthalate, diisobutyl phthalate, di-normal-hexyl phthalate, bis(2-ethylhexyl) phthalate, di-normal-octyl phthalate, di-isononyl phthalate, di-nonyl phthalate, di-isodecyl phthalate, bis-butyl benzyl phthalate, etc.), benzoic acid alkyl ester (e.g., methyl benzoate, ethyl benzoate, propyl benzoate, and butyl benzoate), salicylic acid alkyl ester (e.g., methyl salicylate, ethyl salicylate, propyl salicylate, and butyl salicylate), cinnamic acid alkyl ester (e.g., methyl cinnamate, ethyl cinnamate, propyl cinnamate, and butyl cinnamate), aliphatic carboxylic acid having the carbon number of 8 to 9 and ester thereof, for example, octanoic acid, nonanoic acid, and alkyl ester thereof (e.g., methyl ester, ethyl ester, propyl ester, and butyl ester), and alcohols having the carbon number of 3 to 10, for example, propane-1-ol, butane-1-ol, pentan-1-ol, hexane-1-ol, heptan-1-ol, octan-1-ol, nonane-1-ol, and decane-1-ol.

The water-soluble or amphiphilic organic impurities also having been considered as being difficult to remove may be, for example, hydroquinone, catechol, 4-t-butyleatechol, propanol, butanol, pentanol, hexanol, octanoic acid, nonanoic acid, decanoic acid, dodecanoic acid, perfluorooctanoic acid, $CF_3(CF_2)_6COOH$, $CF_3(CF_2)_3COOH$, $H(CF_2)_8COOH$, $H(CF_2)_{10}COOH$, $CF_3CF_2CF_2OCF(CF_3)CF_2OCF(CF_3)COOH$, and salts thereof.

An amount of the fluorine-containing organic acid contained in the composition may preferably be 0.1 to 60 parts by weight, more preferably 1 to 50 parts by weight, further preferably 5 to 30 parts by weight, based on 100 parts by weight of the composition.

An amount of the impurities contained in the composition may preferably be 0.00005 to 1 part by weight, preferably 0.0001 to 1 part by weight, and more preferably 0.0005 to 1 part by weight, based on 100 parts by weight of the composition. The "impurities" in this description do not include a solvent, or generally water or an aqueous solvent, constituting the composition.

The composition containing a fluorine-containing organic acid and impurities may preferably be a composition having a concentration of a fluorine-containing organic acid increased to, for example, the range described above, by a means such as concentrating a waste liquid containing a fluorine-containing organic acid or recovering a fluorine-containing organic acid from a waste liquid or an intermediate product containing a fluorine-containing organic acid. The waste liquid containing a fluorine-containing organic acid may be, for example, a waste liquid generated or discharged at a step of producing, or a step of using, a fluorine-containing organic acid. The waste liquid generated or discharged at a step of using a fluorine-containing organic acid may be, for example, a waste liquid (aqueous waste liquid) generated by a polymerization reaction of fluoropolymers, etc. The waste liquid comprises a waste liquid generated by washing an exhaust gas containing a fluorine-containing organic acid generated by a polymerization reaction of fluoropolymers, with a wet exhaust gas cleaning device (scrubber). In the process of producing fluoropolymers, the fluorine-containing organic acid is generally used as an emulsifier. Therefore, the waste liquid or the exhaust gas generated by the polymerization reaction contains the fluorine-containing organic acid. The waste liquid generated or discharged at the step of producing a fluorine-containing organic acid may be a waste liquid (aqueous waste liquid) generated by a production step (e.g., a washing step) of the fluorine-containing organic acid etc.

The intermediate product containing a fluorine-containing organic acid may be, for example, a fluoropolymer dispersion liquid that is a reaction product generated in a polymerization reaction process of producing a fluoropolymer. In this description, the "intermediate product" means a reaction product generated by a reaction such as polymerization reaction, which is the product in a state before a treatment such as purification.

Specific examples of the method of concentrating or recovering a fluorine-containing organic acid include, for example:

a method of concentrating (recovering) the fluorine-containing organic acid by performing ultrafiltration of the waste liquid containing the fluorine-containing organic acid;

a method of concentrating (recovering) the fluorine-containing organic acid by performing a filtration treatment using a reverse osmosis membrane for the waste liquid containing the fluorine-containing organic acid;

a method of concentrating (recovering) the fluorine-containing organic acid by adsorbing the waste liquid containing the fluorine-containing organic acid or the intermediate product containing the fluorine-containing organic acid (e.g., a resin dispersion liquid after a polymerization reaction) to an anion-exchange resin (anion-exchange resin treatment);

a method of concentrating (recovering) by contacting the waste liquid containing the fluorine-containing organic acid with highly activated carbon such as activation-treated activated carbon (e.g., steam-activation-treated activated carbon) to adsorb the fluorine-containing organic acid to the highly activated carbon; and a method of concentrating the fluorine-containing organic acid by performing evaporative concentration of the waste liquid containing the fluorine-containing organic acid.

With these treatments, the fluorine-containing organic acid contained in the waste liquid or the intermediate product is recovered, or the concentration of the fluorine-containing organic acid contained in the waste liquid is increased (in this description, these treatments are collectively referred to as "concentrating the fluorine-containing organic acid"). This enables preparation of a composition having the content of the fluorine-containing organic acid of 0.1 to 60 parts by weight based on 100 parts by weight of the composition (a composition preparing step).

For the ultrafiltration, for example, a known ultrafiltration means described in Japanese Patent Application Publication No. S55(1980)-120630 can be usable.

For the filtration treatment using a reverse osmosis membrane, for example, a known filtering means using a reverse osmosis membrane described in Japanese Patent Application Publication No. 2002-58966 can be usable. For the reverse osmosis membrane, for example, a polyamide membrane, a polysulfone membrane, and a polyimide membrane can be usable.

For the treatment with the anion-exchange resin, for example, a known fluorine-containing organic acid separation method using an anion-exchange resin (IER) described in Japanese Patent Application Publication No. 2002-59160 can be usable. The anion-exchange resin may be, for example, an ion-exchange resin having an amino group and/or a quaternary ammonium salt as an ion-exchange group.

The highly activated carbon may be, for example, a known highly activated carbon described in WO 2010/113720. By contacting the waste liquid containing the fluorine-containing organic acid with the highly activated carbon, the fluorine-containing organic acid is adsorbed to the highly activated carbon, so that the fluorine-containing organic acid can be recovered.

For the evaporative concentration, a known evaporative concentration means generally usable by those skilled in the art can be usable.

Known methods other than those described above can also be used. For example, a known cloud point concentration method described in WO 2004/050719 is usable.

These treatments may be each performed once or multiple times and may be performed in combination with one or more treatments.

Flocculant Mixing Step and Separating Step

One aspect of the method of the present invention may be a treatment method of at least partially removing impurities from a composition containing a fluorine-containing organic acid having the carbon number of 2 to 7 and impurities, the method including a flocculant mixing step of mixing the composition and a flocculant, and a separating step of separating a mixed phase obtained at the mixing step into a solid phase and a liquid phase.

The flocculant may be, for example, a metal salt and a polymer flocculant. The flocculant may preferably be a metal salt. For the flocculant that is a metal salt, a metal salt containing a divalent or higher metal element may be preferable. The divalent or higher metal element constituting the metal salt may preferably be one or more metal elements selected from the group consisting of Fe, Al, and Ca. It is more preferable that a counter ion of the metal element constituting the metal salt is one or more counter ions selected from the group consisting of a sulfate ion, a hydroxide ion, a fluoride ion, a nitrate ion, and a chloride ion.

A polymer flocculant may be, for example, sodium alginate, a chitin/chitosan-based flocculant, a cationic polymer flocculant, an anionic polymer flocculant, and a nonionic polymer flocculant and the like.

In this description, the "metal salt" means a simple salt, a double salt, and/or a complex salt. The "salt containing a divalent or higher metal element" means a simple salt, double salt, and/or complex salt containing a divalent or higher metal element.

Specific examples of preferable metal salts are, for example:

aluminum salts (e.g., aluminum sulfate and polyaluminum chloride);

iron salts (e.g., ferrous hydroxide, ferric hydroxide, ferrous sulfate, ferric sulfate, and polyferric sulfate);

calcium salt (e.g., calcium hydroxide, calcium chloride, calcium sulfate, calcium carbonate, calcium nitrate, and calcium fluoride); and silicate minerals (e.g., kaolinite, montmorillonite, zeolite, etc.) containing a divalent or higher metal element and silicon.

A metal salt usable as a flocculant may have a form of generating a metal salt or converting counter ions of a metal element of a metal salt at the flocculent mixing step of mixing the composition and the flocculent. Such a form may be, for example, a form of adding a metal salt (e.g., metal hydroxide) having counter ions other than fluorine into a composition containing fluoride ions. In such a form, conversion of counter ions of a metal salt occurs at the flocculent mixing step. The occurrence of conversion of counter ions of a metal salt may lead to a better impurity removal effect, which is more preferable.

For the flocculant, commercial products may be used. Commercially available flocculants may be Flonite 723, Flonite 113, Flonite 101, Flonite S, Flonite D, and the like, manufactured by Nihon Kassei Hakudo, which are silica alumina flocculants.

An amount of the flocculant to be used can appropriately be selected depending on the kind of the flocculant and the concentration etc. of the fluorine-containing organic acid. The amount of the flocculant may preferably be 0.01 to 10 parts by weight, more preferably 0.05 to 5 parts by weight, based on 100 parts by weight of the composition, for example. A mixing means at the flocculent mixing step may be any mixing means appropriately selectable according to the amount and concentration of the composition, and can be conducted by using a stirring means etc. which is conventionally used.

By separating the mixed phase obtained by mixing the composition and the flocculant into a solid phase and a liquid phase, the impurities contained in the composition are at least partially removed. A separating means can be conducted by using any separating means appropriately selectable according to the amount and concentration of the composition. A specific separating means may be, for example, a separating means that uses filtration using various filters, filtration using a filter aid such as celite or diatomaceous earth, collection of supernatant, decantation, centrifugation, or a solid-liquid separating device (e.g., Laval separator). If filtration is performed, any method of natural filtration, pressure filtration, and suction filtration may be used, or a plurality of separating means may be performed in combination.

At this separating step, the fluorine-containing organic acid having the carbon number of 2 to 7 is present in the liquid phase, and the impurities containing the organic compound having the carbon number of 3 to 50 (e.g., carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50) are at least partially present in the solid phase. More specifically, by mixing the composition and the flocculant, at least a portion of the impurities is flocculated and present in the solid phase. As a result, the impurities can at least partially be removed.

The step described above is extremely preferred as a means of at least partially removing impurities from a composition containing a fluorine-containing organic acid having the carbon number of 2 to 7. For example, if the metal salt is added to a composition containing a fluorine-containing organic acid having the carbon number of 8 or more, an insoluble organic acid salt is formed. The insoluble organic acid salt forms a solid phase at the separating step. Therefore, when the carbon number of the fluorine-containing organic acid is 8 or more, the fluorine-containing organic acid itself is removed together with the impurities. As a result, the concentration (recovery rate) of the fluorine-containing organic acid is reduced. On the other hand, the fluorine-containing organic acid having the carbon number of 2 to 7 does not form an insoluble salt with the metal salt. Therefore, it is advantageous that the impurities can efficiently be removed without reducing the concentration (recovery rate) of the fluorine-containing organic acid.

Contacting Step and Separating Step

Another aspect of the method of the present invention may be a treatment method of at least partially removing impurities from a composition containing a fluorine-containing organic acid having the carbon number of 2 to 7 and impurities, the method including a contacting step of contacting the composition with activated carbon, and a separating step of separating a contacting mixed phase obtained at the above step into a solid phase and a liquid phase.

The activated carbon used at the contacting step may be activated carbon which is conventionally used. Therefore, the activated carbon used at the contacting step is not intended to be highly activated carbon such as steam-activation-treated activated carbon. The highly activated carbon such as steam-activation-treated activated carbon is improved in performance of adsorbing the fluorine-containing organic acid having the carbon number of 2 to 7. On the other hand, the highly activated carbon such as steam-activation-treated activated carbon is not improved in performance of adsorbing the impurities.

The activated carbon used at the contacting step may preferably be activated carbon having a specific surface area of 500 to 1900 $m^2/g$, more preferably activated carbon having a specific surface area of 700 to 1,500 $m^2/g$. The shape of the activated carbon is not particularly limited and may be, for example, a pellet, granular, powdered, or spherical particle shape.

The activated carbon usable in the contacting step may be a commercial product. The commercial product may be, for example, Filtrasorb (trademark) 400, 600 CAL, Diahope (trademark), and Diasorb (trademark) manufactured by Calgon Carbon Japan, the Ebadia series manufactured by Swing Corporation, and the Shirasagi series manufactured by Osaka Gas Chemicals, and the like.

An amount of the activated carbon to be used may preferably be 0.01 to 5 parts by weight, more preferably 0.1 to 3 parts by weight, based on 100 parts by weight of the composition. A contacting means in the activated carbon contacting step may be any contacting means appropriately selectable according to the amount and concentration of the composition, may be conducted by passing a liquid through a tower or a column etc. filled with activated carbon, or can be conducted by using mixing/stirring means etc., which is conventionally used. For the contacting means, a means for passing a liquid through a tower or a column etc. filled with activated carbon is more preferable. In this case, it may be preferable to use the granular or spherical-particle activated carbon. The average particle diameter of the activated carbon may preferably be 0.1 to 5 mm, more preferably 0.5 to 2 mm. The linear speed at the time of passing liquid in the case of passing liquid may preferably be 0.1 to 50 m/h, more preferably 1 to 20 m/h.

The average particle diameter means 50% particle diameter (D50, median diameter). The average particle diameter of the activated carbon can be measured by a sieving method conforming to JIS K1474 (2014), for example.

If the contacting step is performed by mixing and stirring, the impurities contained in the composition are at least partially removed by separating the obtained contacting mixed phase into a solid phase and a liquid phase. A separating means can be conducted by using any separating means appropriately selectable according to the amount and concentration of the composition. A specific separating means may be, for example, a separating means that uses filtration using various filters, collection of supernatant, decantation, centrifugation, or a solid-liquid separating device (e.g., Laval separator).

At this separating step, the fluorine-containing organic acid having the carbon number of 2 to 7 is present in the liquid phase, and the impurities containing the organic compound having the carbon number of 3 to 50 (e.g., carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50) are at least partially present in the solid phase. More specifically, by contacting the composition with the activated carbon, at least a portion of the impurities is adsorbed to the activated carbon and present in the solid phase. As a result, the impurities can at least partially be removed.

The step described above is extremely preferred as a means of at least partially removing impurities from a composition containing a fluorine-containing organic acid having the carbon number of 2 to 7. For example, when activated carbon is contacted with a composition containing a fluorine-containing organic acid having the carbon number of 8 or more, the fluorine-containing organic acid having the carbon number of 8 or more itself is also adsorbed to the activated carbon. On the other hand, the fluorine-containing organic acid having the carbon number of 2 to 7 has low adsorptivity to activated carbon which is conventionally used. Therefore, it is advantageous that by contacting the activated carbon with the composition containing a fluorine-containing organic acid having 2 to 7 carbon atoms, the impurities contained in the composition can selectively and efficiently be adsorbed and removed.

When the composition is passed through a tower or a column etc. filled with activated carbon, the composition is poured into the tower or the column packed with activated carbon to cause contact between the composition and the activated carbon, i.e., to form a contacting mixed phase. The composition subsequently flows out, so that the contacting mixed layer is separated into a solid phase and a liquid phase. In the present invention, a form of passing a composition through a tower or a column etc. filled with activated carbon is included in the treatment method including the contacting step and the separating step. In other words, the contacting step and the separating step may concurrently be performed.

In the present invention, the flocculant mixing step and the subsequent separating step as well as the contacting step and the subsequent separating step may be performed independently of each other or may be performed in combination in any order. When performed in combination, the flocculant mixing step and the subsequent separating step may be followed by the contacting step and the subsequent separating step (second separating step), or the contacting step and the subsequent separating step may be followed by the flocculent mixing step and the subsequent separating step (second separating step).

Flocculant and Activated Carbon Mixing Step, and Separating Step

Another aspect in the present invention may be a treatment method of at least partially removing impurities from a composition containing a fluorine-containing organic acid having the carbon number of 2 to 7 and impurities by a method including a flocculant and activated carbon mixing step of mixing the composition, the flocculant, and the activated carbon, and a separating step of separating a mixed phase obtained at the mixing step into a solid phase and a liquid phase. This aspect is an aspect in which the flocculant mixing step and the contacting step described above are performed at one time and the obtained mixed layer is separated into a solid phase and a liquid phase to at least partially remove the impurities. This aspect can be conducted by using the types and amounts of the flocculant and the activated carbon as well as the various procedures at the mixing and separating steps in the same way as described above.

Other Steps Etc

In the method of the present invention, the liquid phase obtained at the separating step after the mixing step and/or the separating step after the contacting step may be washed. This washing may preferably be an acid washing step of mixing the liquid phase obtained at the separating step with an inorganic acid to perform washing. The inorganic acid usable in the acid washing step may be an inorganic acid that is a strong acid such as sulfuric acid, hydrochloric acid, nitric acid, and phosphoric acid. A sulfuric acid may preferably be used as the inorganic acid. The washing step can be performed, for example, by applying a washing treatment using an aqueous solution containing an inorganic acid (e.g., a sulfuric acid aqueous solution) to a liquid phase (aqueous solution) containing a fluorine-containing organic acid having the carbon number of 2 to 7. The acid washing step can be performed in conformity to known methods described in U.S. Pat. No. 6,281,374 and Japanese Patent Application Publication No. 2006-501300. The acid washing step can at least partially remove, for example, various ionic components (e.g., calcium ions, sodium ions, and fluoride ions), inorganic acids and organic acid components with high water solubility (e.g., nitric acid, hydrochloric acid, oxalic acid, and formic acid).

By using the method of the present invention, impurities can at least partially be removed from a composition containing a fluorine-containing organic acid having the carbon number of 2 to 7. For example, it is found that if a composition is obtained by recovering a fluorocarboxylic acid used as an emulsifier from a waste liquid etc. in a polymerization reaction of fluoropolymers and is used as an emulsifier again in the production of fluoropolymers, the polymerization reaction may not favorably progress. On the other hand, by using the method of the present invention, impurities can effectively be removed from a composition containing a fluorine-containing organic acid having the carbon number of 2 to 7. Consequently, it is advantageous that even the composition (recovered composition) containing a fluorine-containing organic acid having the carbon number of 2 to 7 as described above can preferably be used in the polymerization reaction.

EXAMPLES

The present invention will more specifically be described with the following examples; however, the present invention is not limited thereto. In the examples, "parts" and "%" are based on weight unless otherwise specified.

Example 1

To 100 g of an aqueous solution containing 1200 ppm of fluorine ions, 160 ppm of paraffin (linear alkane having the carbon number of 20 to 40) and 16.0% $CF_3OCF(CF_3)CF_2OCF(CF_3)COONa$, 0.1 g of $Ca(OH)_2$ was added, and 10% sulfuric acid was added to adjust pH to 6 to 9 with stirring, resulting in generation and precipitation of a white solid of $CaF_2$. After the stirring was stopped, the solution was allowed to stand for 3 hours and 50 ml of the supernatant was collected to analyze (i) paraffin and (ii) $CF_3OCF(CF_3)CF_2OCF(CF_3)COONa$ concentrations.
(i) Analysis of Paraffin: Paraffin was extracted from the aqueous solution by using an organic solvent and analyzed by GC (gas chromatography) with an FID detector to measure the paraffin concentration.
(ii) Analysis of $CF_3OCF(CF_3)CF_2OCF(CF_3)COONa$ concentration: The object liquid was diluted 1000 times and HPLC analysis was performed.

The results are shown in Table 1.
The devices and analytical conditions used for the gas chromatographic analysis are as follows:
Gas chromatograph: Agirent 6890
Detector: FID
Sample injection amount: 1 μl
Split ratio: 1/20.
The devices used for the HPLC analysis are as follows:
HPLC Body: Alliance Separation Module 2695 manufactured by Waters
Detector: Waters 2487 detector manufactured by Waters.

Example 2

To 100 g of an aqueous solution containing 40 ppm of paraffin and 9.5% $CF_3OCF(CF_3)CF_2OCF(CF_3)COONa$, 0.5 g of $Ca(OH)_2$ was added and stirred. After the stirring was stopped, filtration was performed by using a suction filter with celite No. 503 manufactured by Celite Corporation placed on filter paper to obtain a filtrate. Paraffin and $CF_3OCF(CF_3)CF_2OCF(CF_3)COONa$ concentrations in the filtrate were analyzed. The results are shown in Table 1.

Example 3

To 100 g of an aqueous solution containing 160 ppm of paraffin and 16.0% $CF_3OCF(CF_3)CF_2OCF(CF_3)COONa$, 1.0 g of Fluorite D manufactured by Nihon Kassei Hakudo was added and stirred. After the stirring was stopped, the solution was allowed to stand for 3 hours and 50 ml of the supernatant was collected to analyze paraffin and $CF_3OCF(CF_3)CF_2OCF(CF_3)COONa$ concentrations. The results are shown in Table 1.

Example 4

To 50 g of an aqueous solution containing 40 ppm of paraffin and 9.5% $CF_3OCF(CF_3)CF_2OCF(CF_3)COONa$, 0.1 g of aluminum sulfate hexadecahydrate was added and stirred. After the stirring was stopped, filtration was performed by using a suction filter with celite placed on filter paper to obtain a filtrate. Paraffin and $CF_3OCF(CF_3)CF_2OCF(CF_3)COONa$ concentrations in the filtrate were analyzed. The results are shown in Table 1.

Example 5

To 400 g of an aqueous solution containing 25% $CF_3(CF_2)_6COONH_4$, 0.2 g of octanol and 0.2 g of linear alkane having the carbon number of 12 to 17 were added and stirred. After stirring for 2 hours, the linear alkane having the carbon number of 12 to 17 was emulsified so that a white turbid aqueous solution, was obtained.

To 200 g of the aqueous solution containing 500 ppm of dispersion of linear alkane having the carbon number of 12 to 17 and 500 ppm of octanol prepared by the method described above, 0.4 g of aluminum sulfate hexadecahydrate was added and stirred, and the solution was adjusted to pH 6 to 9 with a 1 N sodium hydroxide aqueous solution. After the stirring was stopped, the solution was allowed to stand for 2 hours and the supernatant was collected to analyze paraffin and $CF_3(CF_2)_4COONa$ concentrations. The results are shown in Table 1. As a result of concentration analysis of octanol contained in the obtained supernatant by GC, the concentration was 35 ppm.

Comparative Example 1

To 100 ml of an aqueous solution containing 100 ppm of paraffin and 9.1% of $CF_3(CF_2)_6COONa$, 0.5 g of $Ca(OH)_2$ was added and stirred. After the stirring was stopped, the solution was allowed to stand for 3 hours and 50 ml of the supernatant was collected to analyze paraffin and $CF_3(CF_2)_6COONa$ concentration. The results are shown in Table 1.

TABLE 1

|  | Example 1 | Example 2 | Example 3 | Example 4 | Example 5 | Comparative Example 1 |
|---|---|---|---|---|---|---|
| alkane concentration before treatment *1/ppm | 160 | 40 | 160 | 40 | 500 | 100 |
| fluorine-containing carboxylic acid concentration before treatment | 16.0% | 9.5% | 16.0% | 9.5% | 25.0% | 9.1% |
| carbon number of fluorine-containing carboxylic acid | 7 | 7 | 7 | 7 | 6 | 8 |
| flocculent |  | $Ca(OH)_2$ | $Ca(OH)_2$ | Flonite D | $Al_2(SO_4)_3$ | $Al_2(SO_4)_2$ | $Ca(OH)_2$ |
| flocs (main component) | $CaF_2$ | $Ca(OH)_2$ | Flonite D | $Al_2(OH)_3$ | $Al_2(OH)_3$ | PFOA calcium salt |

TABLE 1-continued

|  | Example 1 | Example 2 | Example 3 | Example 4 | Example 5 | Comparative Example 1 |
|---|---|---|---|---|---|---|
| alkane concentration after treatment *1/ppm | <1 | <1 | <1 | <1 | <1 | <1 |
| fluorine-containing carboxylic acid concentration after treatment | 16.0% | 9.6% | 16.0% | 9.5% | 24.8% | 0.4% |
| amount of fluorine-containing carboxylic acid reduced by treatment (%) | <1% | <1% | <1% | <1% | <1% | 96% |

*1: Examples 1 to 4 and Comparative Example 1 mean concentration of paraffin, and Example 5 means concentration of linear alkane.

Example 6

To 60 g of an aqueous solution containing 50% $CF_3(CF_2)_4COONH_4$, 0.1 g of 1-decanol was added and stirred. Subsequently, after 0.03 g of bis(2-ethylhexyl) phthalate (hereinafter referred to as DEHP) was added and stirred, 240 g of water was added and stirred to obtain a white turbid liquid. GC analysis of 1-decanol and DEHP as well as analysis of $CF_3(CF_2)_4COONH_4$ concentration were performed in this white turbid liquid. The results are shown in Table 2.

To 100 g of the white turbid liquid obtained as described above, 0.2 g of aluminum sulfate hexadecahydrate was added and stirred. Subsequently, a 1 mol/L sodium hydroxide aqueous solution was added to adjust pH to 6 to 9 with stirring, resulting in precipitation and sedimentation of aluminum hydroxide. After the stirring was stopped, the solution was allowed to stand for 1 hour, and the supernatant was collected to perform GC analysis of 1-decanol and DEHP as well as analysis of $CF_3(CF_2)_4COONa$ concentration with the same method as described above. The results are shown in Table 2. Analysis of alcohol and phthalic acid ester was performed as in the analysis of paraffin.

Example 7

To 60 g of an aqueous solution containing 50% $CF_3OCF(CF_3)CF_2OCF(CF_3)COONH_4$, 0.03 g of DEHP was added and stirred, and 200 g of water was further added and stirred to obtain a white turbid liquid. Results of GC analysis of DEHP and analysis of carboxylic acid concentration of the white turbid liquid are shown in Table 2. To 100 g of this white turbid liquid, 0.2 g of aluminum sulfate hexadecahydrate was added and stirred. Subsequently, a 1 mol/L sodium hydroxide aqueous solution was added to adjust pH to 6 to 9 with stirring. After the stirring was stopped, the solution was allowed to stand for 1 hour and the supernatant was collected to perform GC analysis of DEHP and analysis of $CF_3OCF(CF_3)CF_2OCF(CF_3)COONH_{14}$ concentration. The results are shown in Table 2.

TABLE 2

|  |  | Example 6 | Example 7 |
|---|---|---|---|
| flocculant |  | aluminum sulfate | aluminum sulfate |
| 1-decanol concentration/ GC Area ppm | before treatment | 2030 | — |
|  | after treatment | 6 | — |
| DEHP concentration/GC Area ppm | before treatment | 220 | 1729 |
|  | after treatment | <1 | 857 |
| carboxylic acid concentration | before treatment | 10.0% | 13.1% |
|  | after treatment | 9.9% | 12.7% |

Example 8

Preparation of Emulsifier Recovery Liquid (Composition Preparing Step)

$CF_3OCF(CF_3)CF_2OCF(CF_3)COONH_3$ was used as an emulsifier to polymerize a fluororesin in the presence of paraffin and a mixture of polyoxyethylene alkyl ether (the carbon number of 12 and 14) and dodecanol was added to a resin dispersion after polymerization, then, a polymer was flocculated and the polymer was dried by a hot-air drier. The air at the exhaust outlet of this dryer was washed with an alkaline aqueous solution to recover the emulsifier, which was then concentrated with a reverse osmosis membrane. In the concentrate, $CF_3OCF(CF_3)CF_2OCF(CF_3)COONa$ was contained in an amount of 10%. As a result of GC analysis of this concentrated aqueous solution with the same method as the analysis of paraffin, the concentration of contained impurities was 1650 ppm (GC area ratio) with respect to the carboxylic acid.

Impurity Removal Process

To 2000 ml of this concentrated solution, 2 g of aluminum sulfate hexadecahydrate was added and stirred. Subsequently, sodium hydroxide was added to adjust pH to 8.5 with stirring. Ten gram of celite was added and filtration was performed by using a suction filter with celite placed on filter paper to obtain a filtrate. As a result of GC analysis of the filtrate with the same method as described above, the concentration of contained impurities was 100 ppm (GC area ratio) with respect to the carboxylic acid.

Example 9

To 100 g of the white turbid liquid prepared in Example 6, 1 g of activated carbon (F-400 manufactured by Calgon Carbon Japan) was added and stirred for 1 hour. After the stirring was stopped, the solution was allowed to stand for 1 hour, and the supernatant was collected to perform the GC analysis of DEHP and 1-decanol as well as the analysis of $CF_3(CF_2)_4COONH_4$ concentration. The results are shown in Table 3. The GC analysis of alcohol and phthalic acid ester was performed as in Example 6.

Example 10

To 60 g of an aqueous solution containing 50% $CF_3OCF(CF_3)CF_2OCF(CF_3)COONH_4$, 0.03 g of 1-decanol was added and stirred. Additionally, 240 g of pure water was added and stirred to obtain a colorless transparent solution. To 100 g of this colorless transparent solution, 1 g of activated carbon (F-400 manufactured by Calgon Carbon Japan) was added and stirred for 1 hour. After the stirring was stopped, the solution was allowed to stand for 1 hour and the supernatant was collected to perform GC analysis of 1-decanol and analysis of $CF_3OCF(CF_3)CF_2OCF(CF_3)COONH_4$ concentration. The results are shown in Table 3.

Comparative Example 2

To 100 ml of an aqueous solution containing 200 ppm of 1-decanol and 10% $CF_3(CF_2)_6COONH_4$, 1 g of activated carbon (F-400 manufactured by Calgon Carbon Japan) was added and stirred for 30 minutes. After the stirring was stopped, filtration was performed with a 0.2 λm filter, and the obtained filtrate was analyzed in terms of hexadecyl alcohol and $CF_3(CF_2)_6COONH_4$ concentration. The results are shown in Table 3.

Example 11

To 200 g of an aqueous solution containing 50% $CF_3(CF_2)_4COONH_4$, 0.5 g of 1-decanol was added and stirred. Subsequently, after 0.1 g of DEHP was added and stirred, 800 g of water was added and stirred to obtain a white turbid liquid. For this white turbid liquid, GC analysis of 1-decanol and DEHP as well as analysis of $CF_3(CF_2)_4COONH_4$ concentration were performed. The results are shown in Table 2. To 1000 ml of the white turbid liquid, 2 g of aluminum sulfate hexadecahydrate was added and stirred. Subsequently, a 1 mol/L sodium hydroxide aqueous solution was added to adjust pH to 6 to 9 with stirring, 10 g of Celite was added, and filtration was performed by using a suction filter with celite placed on filter paper to obtain a filtrate. A column was filled with activated carbon ($F_{400}$ manufactured by Calgon Carbon Japan) and the whole amount of the filtrate obtained earlier was passed therethrough for 3 hours. For the liquid after passing, analysis of 1-decanol, DEHP, and $CF_3(CF_2)_4COONH_4$ concentration was performed. The results are shown in Table 3.

the mixture was placed in a separatory funnel and allowed to stand, and a lower layer (carboxylic acid layer) was extracted. After 100 g of 50% sulfuric acid was added to the extracted carboxylic acid and stirred, the mixture was placed in a separatory funnel and allowed to stand before a lower carboxylic acid layer was extracted, and 20 g of 98% sulfuric acid was added to the carboxylic acid layer and stirred. After 98 g of the obtained dehydrated carboxylic acid was placed in a still of a distiller equipped with a 5-stage Oldershaw column and the still temperature was heated to 92° C. at normal pressure, a degree of decompression was gradually reduced to 35 mmHg to distill the carboxylic acid, and the distillation was terminated when the distillation volume was 89 g. The still temperature and the top temperature during distillation were substantially constant. When the carboxylic acid obtained by distillation was analyzed by HPLC, the purity of the carboxylic acid was 99% or more, and when the carboxylic acid was analyzed by GC as described above, the amount of detected impurities was 0.5 ppm (GC area ratio) with respect to the carboxylic acid.

By neutralizing 80 g of this carboxylic acid with ammonia water and adding water to adjust concentration, 166 g of a 50% carboxylic acid ammonium salt aqueous solution was obtained.

Example 13

To 100 ml of an emulsifier recovery liquid (carboxylic acid concentration: 10.0%, impurity concentration: 1650 ppm) prepared with the same method as in Example 8, 0.5 g of calcium hydroxide and 2 g of powdered activated carbon (neutral) for column chromatograph were added and stirred for 1 hour. This liquid was filtered by using a 1 μm filter with celite placed thereon to obtain 96 g of filtrate. GC measurement of carboxylic acid concentration and impurities of the filtrate was performed. The carboxylic acid

TABLE 3

|  |  | Example 9 | Example 10 | Example 11 | Comparative Example 2 |
|---|---|---|---|---|---|
| carbon number of carboxylic acid |  | 6 | 7 | 6 | 8 |
| 1-decanol concentration/GC | before treatment | 2030 | 540 | 2100 | 500 |
| Area ppm | after treatment | 17 | 2.7 | <1 | 1.5 |
| DEHP concentration/GC | before treatment | 220 | — | 227 | — |
| Area ppm | after treatment | <1 | — | <1 | — |
| Carboxylic acid | before treatment | 10.0% | 6.8% | 9.9% | 10.0% |
| concentration | after treatment | 9.5% | 6.3% | 9.6% | 8.5% |
| amount of fluorine-containing carboxylic acid reduced by activated carbon treatment (%) |  | 5% | 7.3% | 3% | 15% |

Example 12

A column was filled with activated carbon ($F_{400}$ manufactured by Calgon Carbon Japan), and 1,000 ml of the liquid (impurity concentration: 100 ppm) subjected to the impurity removal process in Example 8 was passed through the column for 3 hours. After 100 g of 98% sulfuric acid was added to the liquid after passing and stirred, the liquid was put in a separatory funnel and allowed to stand, and a lower layer was extracted to obtain 111 g of crude carboxylic acid. After 70 g of 10% sulfuric acid was added to the crude carboxylic acid (containing about 10% of water) and stirred, concentration after treatment was 9.1%. The impurity concentration was 0.4 ppm with respect to the carboxylic acid.

Example 14

To 1000 g of pure water, about 1 g each of $CF_3(CF_2)_4COONa$, $CF_3OCF(CF_3)CF_2OCF(CF_3)COONa$, $CF_3(CF_2)_6COONa$ was added and the carboxylic acid concentration was measured by HPLC. To this aqueous solution, 15.9 g of iron sulfate heptahydrate was added as a flocculant and stirred. A brown precipitate was settled when allowed to stand. The supernatant was filtered through a 0.2 μm filter and analyzed by HPLC. The results are shown in Table 4.

TABLE 4

| carboxylic acid | $CF_3(CF_2)_4COONa$ | $CF_3OCF(CF_3)CF_2OCF(CF_3)COONa$ | $CF_3(CF_2)_6COONa$ |
|---|---|---|---|
| carbon number of carboxylic acid | 6 | 7 | 8 |
| concentration before treatment (ppm) | 973 | 953 | 1063 |
| concentration after treatment (ppm) | 964 | 946 | 72 |

INDUSTRIAL APPLICABILITY

According to the method of the present invention, impurities can more effectively be removed from a composition containing a fluorine-containing organic acid. According to the method of the present invention, for example, even a fluorine-containing organic acid obtained by recovery can preferably be used in various uses (e.g., polymerization reaction).

The invention claimed is:

1. A treatment method of at least partially removing impurities from a composition containing a fluorine-containing organic acid having the carbon number of 2 to 7 and impurities, the method comprising:
   a flocculant mixing step of mixing the composition and a flocculant; and
   a separating step of separating a mixed phase obtained at the mixing step into a solid phase containing the impurities and a liquid phase containing the fluorine-containing organic acid having the carbon number of 2 to 7.

2. A treatment method of at least partially removing impurities from a composition containing a fluorine-containing organic acid having the carbon number of 2 to 7 and impurities, the method comprising:
   a contacting step of contacting the composition with activated carbon, to adsorb at least a part of the impurities to the activated carbon; and
   a separating step of separating a contacting mixed phase obtained at the step into a solid phase containing the impurities and a liquid phase containing the fluorine-containing organic acid having the carbon number of 2 to 7.

3. The method according to claim 1, further comprising after the separating step,
   a contacting step of contacting the liquid phase obtained at the separating step with activated carbon, and
   a second separating step of separating the contacting mixed phase obtained at the step into a solid phase containing the impurities and a liquid phase containing the fluorine-containing organic acid having the carbon number of 2 to 7.

4. A treatment method of at least partially removing impurities from a composition containing a fluorine-containing organic acid having the carbon number of 2 to 7 and impurities, the method comprising:
   a flocculant and activated carbon mixing step of mixing the composition, a flocculant, and activated carbon; and
   a separating step of separating a mixed phase obtained at the mixing step into a solid phase containing the impurities and a liquid phase containing the fluorine-containing organic acid having the carbon number of 2 to 7.

5. The method according to claim 1, wherein the impurities contain an organic compound having the carbon number of 3 to 50.

6. The method according to claim 1, wherein the impurities contain one or more selected from a carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50.

7. The method according to claim 1, wherein the flocculant is a metal salt containing a divalent or higher metal element.

8. The method according to claim 7, wherein the divalent or higher metal element constituting the metal salt is one or more metal elements selected from the group consisting of Fe, Al, and Ca.

9. The method according to claim 7, wherein the metal salt includes as a counter ion of the metal element one or more selected from the group consisting of a sulfate ion, a hydroxide ion, a fluoride ion, a nitrate ion, and a chloride ion.

10. The method according to claim 1, wherein
    the fluorine-containing organic acid is one or more selected from the group consisting of a fluorine-containing carboxylic acid represented by Formula (i):

X—Rf—COOH (i)

[wherein X is H, F, or Cl, Rf is a linear or branched fluoroalkylene group having the carbon number of 1 to 6, a group having the carbon number of 1 to 6 having a monooxyfluoroalkylene group, or a group having the carbon number of 1 to 6 having a polyoxyfluoroalkylene group] and salts thereof.

11. The method according to claim 10, wherein in Formula (i), X is H or F, and Rf is a group having the carbon number of 1 to 6 having a monooxyfluoroalkylene group, or a group having the carbon number of 1 to 6 having a polyoxyfluoroalkylene group.

12. The method according to claim 1, wherein an amount of the fluorine-containing organic acid contained in the composition is 0.1 to 60 parts by weight based on 100 parts by weight of the composition.

13. The method according to claim 1, wherein an amount of the impurities contained in the composition is 0.00005 to 1 part by weight based on 100 parts by weight of the composition.

14. The method according to claim 1, further comprising an acid washing step of mixing the liquid phase obtained at the separating step with an inorganic acid to perform washing.

15. The method according to claim 3, further comprising an acid washing step of mixing the liquid phase obtained at the second separating step with an inorganic acid to perform washing.

16. A treatment method of at least partially removing impurities from a composition containing a fluorine-containing organic acid having the carbon number of 2 to 7 and impurities, the method comprising:

a composition preparing step of preparing a composition in which a content of the fluorine-containing organic acid is 0.1 to 60 parts by weight based on 100 parts by weight of the composition, by concentrating the fluorine-containing organic acid with a means selected from the group consisting of ultrafiltration, reverse osmosis membrane concentration, anion-exchange resin treatment, activation-treated activated carbon treatment, and evaporative concentration for a waste liquid or an intermediate product generated or discharged at a step of producing, or a step of using, the fluorine-containing organic acid;

a flocculant mixing step of mixing the composition and a flocculant;

a separating step of separating a mixed phase obtained at the mixing step into a solid phase containing the impurities and a liquid phase containing the fluorine-containing organic acid having the carbon number of 2 to 7;

a contacting step of contacting the liquid phase obtained at the separating step with activated carbon;

a second separating step of separating a contacting mixed phase obtained at the preceding step into a solid phase containing the impurities and a liquid phase containing the fluorine-containing organic acid having the carbon number of 2 to 7; and an acid washing step of mixing the liquid phase obtained at the second separating step with an inorganic acid to perform washing, wherein the flocculant is a metal salt containing a divalent or higher metal element, and wherein the impurities contain one or more selected from a carboxylic acid having the carbon number of 8 to 50 and derivatives thereof, hydrocarbon having the carbon number of 8 to 50, phenol having the carbon number of 6 to 50, alcohol having the carbon number of 3 to 30, and polyether having the carbon number of 8 to 50.

17. The method according to claim 2, wherein the impurities contain an organic compound having a carbon number of 3 to 50.

18. The method according to claim 2, wherein the impurities contain one or more selected from a carboxylic acid having a carbon number of 8 to 50 and derivatives thereof, hydrocarbon having a carbon number of 8 to 50, phenol having a carbon number of 6 to 50, alcohol having a carbon number of 3 to 30, and polyether having a carbon number of 8 to 50.

19. The method according to claim 2, wherein the fluorine-containing organic acid is one or more selected from the group consisting of a fluorine-containing carboxylic acid represented by Formula (i):

$$X\text{—}Rf\text{—}COOH \qquad (i)$$

[wherein X is H, F, or Cl, Rf is a linear or branched fluoroalkylene group having the carbon number of 1 to 6, a group having the carbon number of 1 to 6 having a monooxyfluoroalkylene group, or a group having the carbon number of 1 to 6 having a polyoxyfluoroalkylene group] and salts thereof.

20. The method according to claim 19, wherein in Formula (i), X is H or F, and Rf is a group having a carbon number of 1 to 6 having a monooxyfluoroalkylene group, or a group having a carbon number of 1 to 6 having a polyoxyfluoroalkylene group.

* * * * *